(12) United States Patent
Krivonos et al.

(10) Patent No.: US 7,776,852 B2
(45) Date of Patent: Aug. 17, 2010

(54) PROCESS FOR PRODUCING HIGHLY PURE MIDAZOLAM AND SALTS THEREOF

(75) Inventors: Sonia Krivonos, Beer Sheva (IL); Yana Sery, Beer Sheva (IL)

(73) Assignee: CHEMAGIS Ltd., Bnei Brak (IL)

( * ) Notice: Subject to any disclaimer, the term of this patent is extended or adjusted under 35 U.S.C. 154(b) by 191 days.

(21) Appl. No.: 11/853,186

(22) Filed: Sep. 11, 2007

(65) Prior Publication Data

US 2009/0069306 A1 Mar. 12, 2009

(51) Int. Cl.
*A61P 25/00* (2006.01)
*A61K 31/5517* (2006.01)
*C07D 487/04* (2006.01)

(52) U.S. Cl. ...................................... 514/220; 540/562
(58) Field of Classification Search ................ 514/220; 540/562
See application file for complete search history.

(56) References Cited

U.S. PATENT DOCUMENTS

| 4,280,957 | A | 7/1981 | Walser et al. |
| 6,262,260 | B1 * | 7/2001 | Dhaon ........................ 540/562 |
| 6,512,114 | B1 | 1/2003 | Dhaon et al. |

* cited by examiner

*Primary Examiner*—Brenda L Coleman
(74) *Attorney, Agent, or Firm*—Leydig, Voit & Mayer, Ltd.

(57) ABSTRACT

Provided is a process for producing highly pure midazolam and salts thereof, and a pharmaceutical composition containing the highly pure midazolam and/or a salt thereof.

17 Claims, No Drawings

PROCESS FOR PRODUCING HIGHLY PURE MIDAZOLAM AND SALTS THEREOF

BACKGROUND OF THE INVENTION

Midazolam (8-chloro-6-(2-fluorophenyl)-1-methyl-4H-imidazo[1,5-a][1,4]benzodiazepine) is represented by the following structural formula (I):

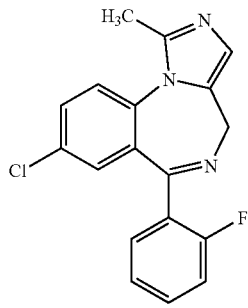

Midazolam is a central nervous system (CNS) depressant, used for short term treatment of insomnia. Like other benzodiazepines, midazolam binds to benzodiazepine receptors in the brain and spinal cord and is thus used as a short-acting hypnotic-sedative drug with anxiolytic and amnestic properties. It is currently used in dentistry, cardiac surgery, endoscopic procedures, as a preanesthetic medication, as an adjunct to local anesthesia and as a skeletal muscle relaxant. Depending on the pH value, midazolam can exist in solution as a closed ring form (I) as well as an open ring form (IA), which are in equilibrium, as shown in Scheme 1:

Scheme 1

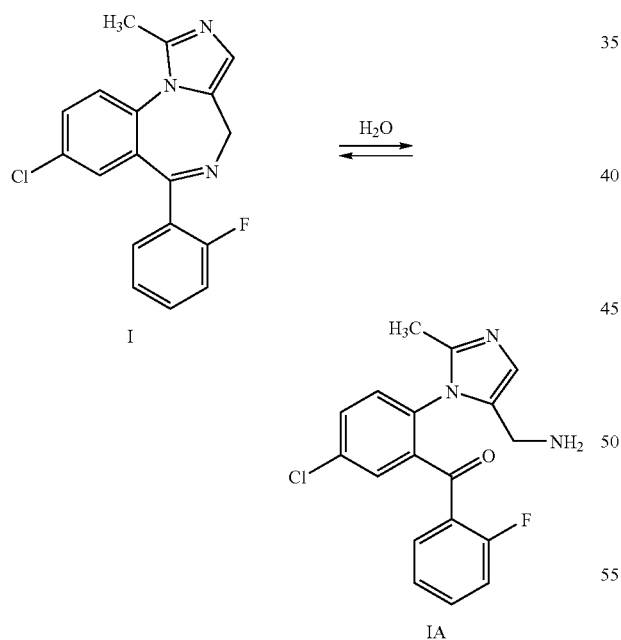

The amount of the open ring form (IA) is dependent upon the pH value of the solution. At a pH value of about 3, the content of the open ring form (IA) can be 40%, while at pH value of 7.5, the closed ring form (I) can be more than 90%.

Clinical studies have demonstrated that there are no significant differences in the clinical activity between midazolam hydrochloride and midazolam maleate, however the use of intravenous midazolam hydrochloride has been associated, in some cases, with respiratory depression and arrest.

U.S Pat. No. 4,280,957 (hereinafter the '957 patent) describes a synthetic process for preparing midazolam, which is depicted in Scheme 2 below. This process includes reacting 2-aminomethyl-7-chloro-2,3-dihydro-5-(2-fluorophenyl)-1H-1,4-bezodiazepine (II) with acetic anhydride in dichloromethane to produce 2-acetamido-methyl-7-chloro-2,3-dihydro-5-(2-fluorophenyl)-1H-1,4-bezodiazepine (III). The latter is heated with polyphosphoric acid at 150° C. to produce 8-chloro-6-(2-fluorophenyl)-3a,4-dihydro-1-methyl-4H-imidazo[1,5-a][1,4]benzodiazepine of formula (IV), which is purified by column chromatography. Compound IV is then mixed with toluene and manganese dioxide and heated to reflux to afford midazolam base, which is crystallized from ether to yield a product with mp of 152-154° C.

Scheme 2

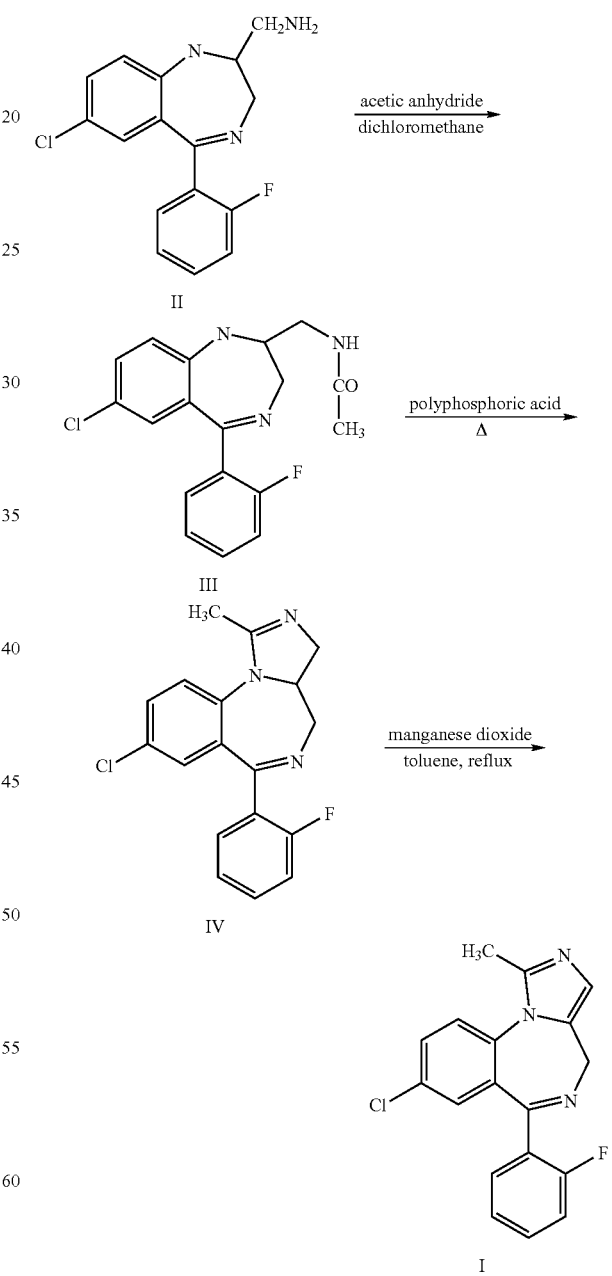

The '957 patent further describes an alternative process which includes reacting 2-aminomethyl-7-chloro-2,3-dihydro-5-(2-fluorophenyl)-1H-1,4-bezodiazepine (II) (optionally as a dimaleate salt) with triethylorthoacetate in ethanol and in the presence of p-toluenesulfonic acid to afford 8-chloro-6-(2-fluorophenyl)-3a,4-dihydro-1-methyl-4H-imidazo[1,5-a][1,4]benzodiazepine (IV). This product is dissolved in xylene and treated with activated manganese dioxide to afford the crude base, which is reacted in situ with maleic acid in ethanol and crystallized by addition of ether to produce the midazolam maleate having melting point of 148-151° C. The process is depicted in Scheme 3 below.

is decarboxylated, followed by treatment with potassium tert-butoxide, to afford midazolm (I), isomidazolam (VI) and a midazolam dimmer (VII). Midazolam base is obtained in 54.5% yield after two re-crystallizations from ethyl acetate and heptane; however, the purity of the product is not disclosed.

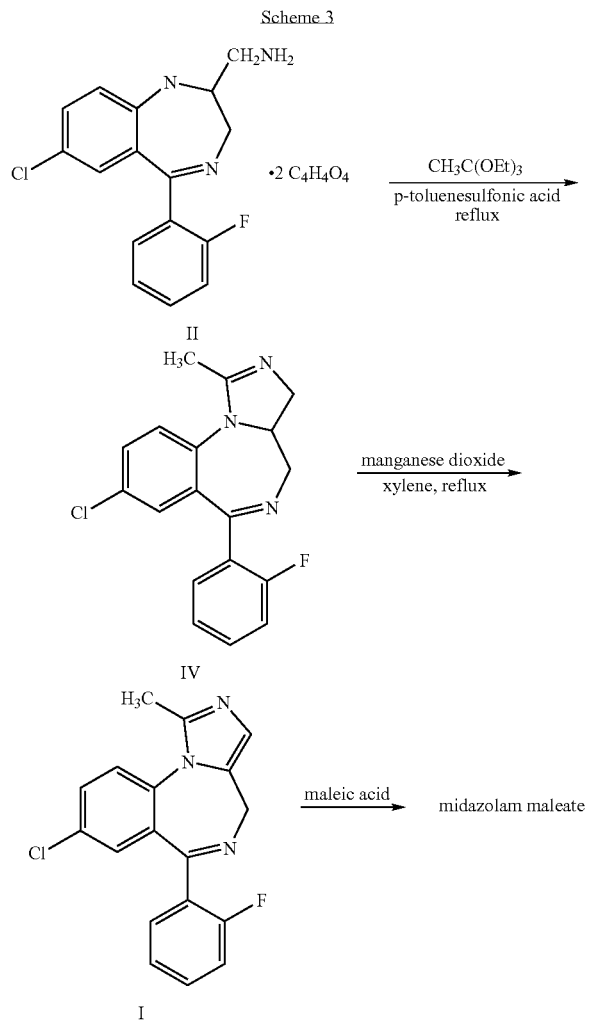

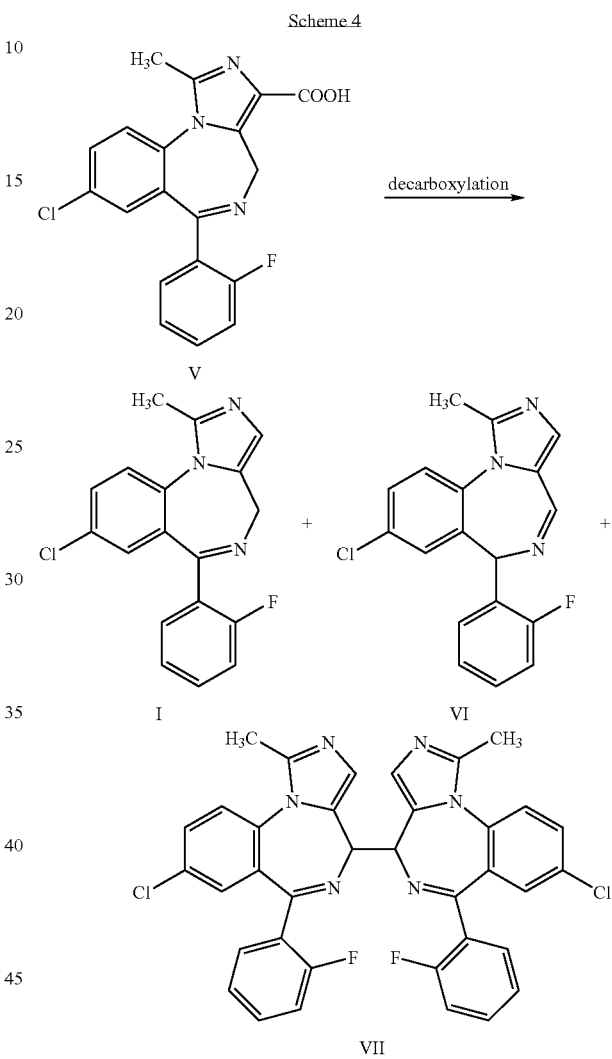

The preparation of midazolam maleate from the isolated midazolam base is also described in a further example of the '957 Patent, wherein a warm solution of midazolam base in ethanol is combined with a warm solution of maleic acid in ethanol. The mixture is diluted with ether and at least part of the solvents is evaporated using a steam bath to obtain crystalline midazolam maleate having melting point of 148-151° C. The yield and the purity of the obtained midazolam maleate are not disclosed.

U.S. Pat. No. 6,512,114 (hereinafter the '114 patent) describes another synthetic process for preparing midazolam, which is depicted in Scheme 4 below. According to this Process, the starting material 8-chloro-6-(2-fluorophenyl)-1-methyl-4H-imidazo[1,5-a][1,4]benzodiazepine-3-carboxylic acid (V) is heated in mineral oil for 3 hours at 230° C. until it The preparation of midazolam by conventional routes is liable to produce impurities such as isomidazolam (VI) and a midazolam dimmer (VII), and possibly other impurities. There is, therefore, a need in the art for a midazolam purification process that will provide highly pure midazolam containing minimal amounts of impurities produced. The present invention provides such a process.

BRIEF SUMMARY OF THE INVENTION

While searching for an improved process for producing midazolam, the inventors of the present invention have found that crude midazolam base, obtained according to conventional synthesis (e.g., as described in Reference Example 1), contains substantial levels of certain impurities, which are not readily removable. These impurities include, e.g., 8-chloro-6-phenyl-1-methyl-4H-imidazo[1,5-a][1,4]benzodiazepine of formula VIII and 8-chloro-6-(2-fluorophenyl)-1-ethyl-4H-imidazo[1,5-a][1,4]benzodiazepine of formula IX.

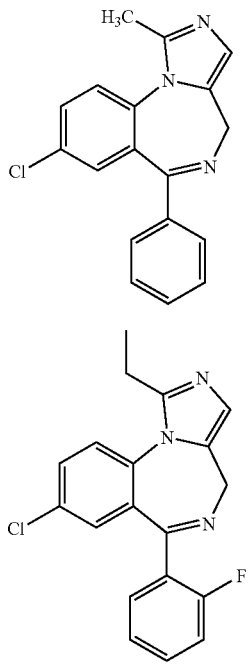

Those skilled in the art will appreciate that the purification of crude midazolam, which contains impurities VIII and/or IX (i.e., compounds VIII and/or IX), and particularly the selective removal of such impurities from crude midazolam without chromatography, would be expected to be especially difficult in view of the very close structural similarities between these compounds and midazolam.

Consistent with this hypothesis, the present inventors have found that precipitation or crystallization of midazolam from solvents such as, e.g., DMSO, DMF, THF, acetone and aqueous mixtures thereof produced either unacceptably low yields (e.g., less than 10%) or failed to substantially reduce the level of impurity VIII. Although such solvents dissolve midazolam well, e.g., at elevated temperature, and allow the midazolam to precipitate upon cooling, the midazolam thus obtained is not readily purified and, in most cases, the precipitated or crystallized midazolam base was found to still contain significant quantities of compound VIII. Such solvents thus were found to be unsuitable for removing the identified impurities. The present inventors also found that converting the crude midazolam base to the maleate salt and precipitating the midazolam maleate failed to substantially remove impurity VIII.

Surprisingly, however, the inventors of the present invention have discovered that by using a solvent mixture containing water and a $C_{1-3}$ alkyl acetate, such as, e.g., methyl acetate or ethyl acetate, it is possible to substantially remove impurity VIII from midazolam while obtaining good yield of midazolam base in relatively high purity. Also surprisingly, it was discovered that substantially removing impurity VIII as described herein does not substantially remove impurity IX (e.g., as shown in Example 1, where the crystallized base can still contain 0.34% impurity IX after impurity VIII is substantially removed); however, once impurity VIII is substantially removed, compound IX can then be readily removed from the resulting product by conversion to the maleate salt (e.g., as shown in Table 2). Thus, in accordance with the present invention, highly pure midazolam maleate can be obtained by substantially removing impurity VIII from a crude midazolam base with a solvent mixture containing water and a $C_{1-3}$ alkyl acetate, converting the resulting midazolam base into the maleate salt to substantially remove impurity IX, and isolating the maleate salt. The process of the present invention can produce highly pure midazolam maleate, e.g., having a purity of at least about 99.8%.

In one embodiment, the present invention provides a process for purifying midazolam base that contains an impurity of formula VIII, an impurity of formula IX, or any combination of such impurities, wherein the process includes: (a) contacting the midazolam base with a solvent containing water and a $C_{1-3}$ alkyl acetate to substantially remove the impurity of formula VIII from the midazolam base; (b) converting the midazolam base produced in step (a) into the maleate salt and isolating the midazolam maleate; and (c) optionally purifying the midazolam maleate produced in step (b), to substantially remove any of impurity IX that may exist. The process of the present invention can produce highly pure midazolam maleate. If desired, the midazolam maleate produced in step (b) or (c) can, in turn, be used as a precursor for producing highly pure midazolam base and other midazolam salts (e.g., midazolam hydrochloride).

Step (a) can include, for example, dissolving the crude midazolam base, which can be obtained by any method known in the art, e.g., by the process described in Reference Example 1, in a solvent containing water and a $C_{1-3}$ alkyl acetate at elevated temperature; allowing the solution to cool sufficiently to precipitate midazolam base (e.g., in the form of crystals); and collecting the thus formed precipitate, e.g., by filtration and, optionally, washing and/or drying the precipitate.

Step (b) can include, for example, dissolving the midazolam base produced in step (a) in a solvent or a solvent mixture, e.g., at elevated temperature; adding maleic acid, e.g., as a solution in an organic solvent, to produce midazolam maleate; allowing the solution to cool sufficiently to precipitate midazolam maleate (e.g., in the form of crystals); and collecting the precipitate, e.g., by filtration and, optionally, washing and/or drying the precipitate.

The purified midazolam maleate obtained as described herein has a purity of at least 98%, and preferably has a purity of at least about 99.5%, and more preferably has a purity of at least about 99.8%. The purified midazolam maleate obtained as described herein preferably contains less than 0.1% each of compounds VIII and IX.

DETAILED DESCRIPTION OF THE INVENTION

The present invention provides a process for purifying midazolam base that contains an impurity of formula VIII (e.g., about 0.3% of impurity VIII or greater by HPLC), an impurity of formula IX (e.g., about 1% of impurity IX or more, by HPLC), or any combination of these impurities. In one embodiment, the process includes: (a) contacting the midazolam base with a solvent containing water and a $C_{1-3}$ alkyl acetate to substantially remove the impurity of formula VIII from the midazolam base; (b) converting the midazolam produced in step (a) into the maleate salt and isolating the midazolam maleate; and (c) optionally purifying the midazolam maleate produced in step (b), to substantially remove any of impurity IX that may be present. The process of the present invention can produce highly pure midazolam maleate. If desired, the highly pure midazolam maleate can be used for producing highly pure midazolam base or other midazolam salts (e.g., midazolam hydrochloride). The molecular structures of impurities VIII and IX are as follows.

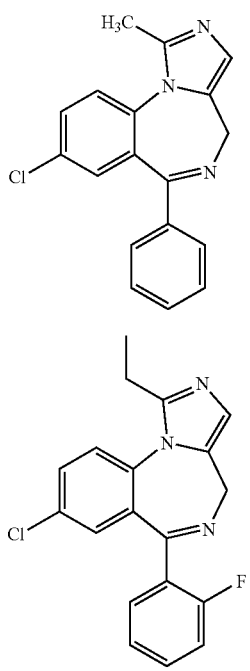

Further purification of the midazolam maleate produced in step (b), e.g., as in step (c), may be desirable in certain cases where the midazolam maleate has a relatively high content of impurity IX. Step (c) can include, e.g., purifying the midazolam maleate by one or more conventional processes such as, e.g., crystallization, precipitation, slurrying or any combination thereof.

Step (a) can be carried out in any suitable manner such as, e.g., precipitation, crystallization, slurrying, washing, dissolution and re-precipitation by addition of a solvent in which the midazolam base is insoluble, or by any combination of such methods. Step (a) can include, for example, dissolving the crude midazolam base, which can be obtained by any method known in the art, e.g., by the process described in Reference Example 1, in a solvent containing water and a $C_{1-3}$ alkyl acetate at elevated temperature; allowing the solution to cool sufficiently to precipitate midazolam base (e.g., in the form of crystals); and collecting the thus formed precipitate, e.g., by filtration and, optionally, washing and/or drying the precipitate, to remove at least a substantial portion of impurity VIII (e.g., to produce midazolam base that is substantially free of impurity VIII).

The $C_{1-3}$ alkyl acetates used in step (a) can include, e.g., methyl acetate, ethyl acetate, isopropyl acetate and mixtures thereof.

Particularly preferred solvents for use in step (a) include mixtures of water and ethyl acetate, and mixtures of water and methyl acetate, which are capable of substantially removing impurity VIII.

Preferably, the ratio between the crude midazolam base and the solvent used in step (a) is from, e.g., about 1 g crude midazolam base per about 1 ml solvent, to, e.g., about 1 g midazolam base per about 7 ml solvent.

Exemplary solvents that can be used for washing precipitated (e.g., crystalline) midazolam base obtained in step (a) include, e.g., acetone, tetrahydrofuran (THF), methyl acetate, ethyl acetate, isopropyl acetate, n-butyl acetate, isobutyl acetate, cyclohexane, and mixtures thereof. Preferred solvents for washing the precipitated midazolam base obtained in step (a) include mixtures of cyclohexane and methyl acetate. In such solvent systems, the cyclohexane:methyl acetate ratio used for washing the precipitated midazolam base can vary, e.g., from about 10:1 (v/v) cyclohexane:methyl acetate to about 1:1 (v/v) cyclohexane:methyl acetate, e.g., about 3:1 (v/v), 2:1 (v/v) cyclohexane:methyl acetate, 1.5:1 (v/v) cyclohexane:methyl acetate, and the like. An exemplary solvent mixture for washing midazolam base produced in step (a) includes cyclohexane:methyl acetate in a ratio of about 2.33:1 (7:3) (v/v).

The midazolam base produced in step (a) preferably contains less than 0.2% of impurity VIII, and more preferably more preferably contains less than about 0.1% of impurity VIII, e.g., less than about 0.07% of impurity VIII.

Step (b) can include, for example, dissolving the midazolam base produced in step (a) in a solvent or a solvent mixture, e.g., at elevated temperature; adding maleic acid, e.g., as a solution in a solvent, which can include an organic solvent, to produce midazolam maleate; allowing the solution to cool sufficiently to precipitate midazolam maleate (e.g., in the form of crystals); and collecting the precipitate, e.g., by filtration and, optionally, washing and/or drying the precipitate.

Solvents that can be used for dissolving the midazolam base in step (b) can include, for example, water, methanol, ethanol, 1-propanol, 2-propanol, 1-butanol, 2-butanol, acetone, tetrahydrofuran (THF) and mixtures thereof. A preferred solvent for dissolving the midazolam base in step (b) is a mixture of THF and water. In such solvent systems, the THF:water ratio can vary, e.g., from about 30:1 (v/v) THF:water to about 1:1 (v/v) THF:water, e.g., about 25:1 (v/v) THF:water, about 20:1 (v/v) THF:water, and the like. An exemplary solvent for dissolving the midazolam base in step (b) is a mixture of THF and water in a ratio of about 25:1 (v/v) THF:water.

Solvents that can be used for adding maleic acid as a solution in step (b) can include organic solvents such as, e.g., methanol, ethanol, 1-propanol, 2-propanol, 1-butanol, 2-butanol, tetrahydrofuran (THF), 2-methyltetrahydrofuran, acetonitrile, N,N-dimethylformamide (DMF), dimethylacetamide (DMA), dimethylsulfoxide (DMSO), and mixtures thereof. A preferred solvent for dissolving and adding maleic acid as a solution in step (b) is THF.

Step (c) can include any purification method known in the art that is suitable for purifying midazolam maleate, e.g., slurrying the midazolam maleate in a suitable solvent (which can include a mixture of solvents), precipitating or crystallizing the midazolam maleate from a suitable solvent (which can include a mixture of solvents), and the like.

The midazolam maleate obtained in step (b) or (c) preferably has a purity of at least 98%, and more preferably has a purity of at least about 99.5%, and most preferably has purity of at least about 99.8%.

The midazolam maleate obtained in step (b) or (c) preferably contains minimal amounts of impurities VIII and IX, e.g., less than about 0.1% of either impurity VIII or IX.

If desired, the midazolam maleate produced in accordance with the process of the present invention can, in turn, be used as a precursor for producing highly pure midazolam base and other highly pure midazolam salts (e.g., midazolam hydrochloride).

The midazolam maleate produced in accordance with the present invention, or the midazolam base or other midazolam salts produced therefrom in accordance with the present invention, can be used in a pharmaceutical composition. The pharmaceutical composition can include therapeutically effective amount of midazolam maleate produced as described herein, or of midazolam base or other indazolam salts produced therefrom as described herein, and a pharmaceutically acceptable carrier, which can include one or more pharmaceutically acceptable additives and/or excipients.

The following examples illustrate the practice of the present invention in some of its embodiments, but should not be construed as limiting the scope of the invention. Other embodiments will be apparent to one skilled in the art from consideration of the specification and examples.

EXAMPLES

Instruments and Methods

HPLC Parameters

| Column: | Phenomenex Luna C18 (2), 250 * 4.6 mm |
|---|---|
| Mobile phase: | A: water, B: acetonitrile |
| UV detector: | 254 nm |
| Flow rate: | 1.0 ml/minute |
| Temperature: | 22° C. |
| Injection volume: | 5 microliter |

Gradient:

| Time, minutes | % A | % B |
|---|---|---|
| 0 | 55 | 45 |
| 20 | 40 | 60 |
| 25 | 40 | 60 |
| 35 | 20 | 80 |
| 35.1 | 55 | 45 |
| 45 | 55 | 45 |

Mass Spectrometry (MS) Parameters

| Source Type: | ESI |
|---|---|
| Capillary temperature, ° C.: | 250 |
| Sheath Gas Flow: | 30 |
| Aux. Gas Flow: | 60 |
| Mode: | Positive polarity |

Reference Example 1

This example describes the preparation of midazolam base as taught in the '957 patent.

16 g (0.03 mol) of 2-aminomethyl-7-chloro-5-(2-fluorophenyl)-2,3-dihydro-1H-1,4-bezodiazepine dimaleate was dissolved in 200 ml of toluene and 10 ml of 25% ammonium hydroxide solution was added and mixing was maintained for an hour. Then, the phases were separated and the toluene phase was dried by azeotropic distillation using a Dean Stark apparatus. 7 ml (0.038 mol) of triethylorthoacetate was added and the solution was heated to reflux for 4 hours, after which time the solution was left to cool to ambient temperature. 25 ml of methyl tert-butyl ether was added and the mixture was cooled overnight to produce 8-chloro-6-(2-fluorophenyl)-3a,4-dihydro-1-methyl-4H-imidazo[1,5-a][1,4]benzodiazepine, which was isolated by filtration. The product was mixed with 200 ml of toluene and dried by azeotropic distillation using a Dean Stark apparatus. Then, 30 g of manganese dioxide was added and the mixture was heated to reflux for two hours. The excess manganese dioxide was filtered off to afford a solution of midazolam base in toluene, which was evaporated to obtain a product having 97.9% purity and containing 0.44% of impurity VIII and 1.14% of impurity IX (according to HPLC).

Example 1

This example describes the purification of midazolam base from a solvent mixture that includes water and methyl acetate.

A reaction vessel was charged with a solution of 6.65 g of crude midazolam base containing 0.32% of Compound VIII and 1.02% of Compound XI (by HPLC), and 33.2 ml of a 3/2 (v/v) solvent mixture comprising methyl acetate and water was added. The mixture was agitated for 12 hours, during which time precipitation occurred. The thus formed crystals were filtered off and washed with 5 ml of cold 7/3 (v/v) mixture of cyclohexane and methyl acetate and dried under vacuum to afford 4.5 g of the crystalline midazolam base in 67.6% yield, having a purity of 99.4% and containing 0.06% of compound VIII and 0.34% of Compound XI (according to HPLC).

Examples 2-3

The following examples describe the crystallization of crude midazolam base from different solvents or solvent mixtures, as detailed in Table 1.

A reaction vessel was charged with 5 g of crude midazolam base and a solvent or solvent mixture as detailed in Table 1 was added. The mixture was heated to reflux and then it was allowed to cool to ambient temperature and agitated for 10 hours, during which time precipitation occurred. The thus formed crystals were filtered off and washed with 5 ml of the cold solvent or solvent mixture as detailed in Table 1 and dried under vacuum to afford the crystalline midazolam base in the yield as detailed in Table 1. The content (%) of compound VIII is based on HPLC.

TABLE 1

| Entry | Solvent, or solvent mixture | Solvent/solid ratio ml/g | % of VIII before crystallization | % of VIII after crystallization | Yield % |
|---|---|---|---|---|---|
| 2 | Isopropyl acetate/H$_2$O (4/1) | 5/1 | 0.25 | 0.10 | 73.8 |
| 3 | Ethyl acetate/H$_2$O (3/2) | 5/1 | 0.36 | 0.08 | 67.7 |

Example 4

This example describes the preparation of midazolam maleate.

2 g of the crystallized midazolam base, containing 0.039% of compound VIII and 0.464% of compound IX (according to HPLC), was dissolved in a mixture of 0.4 ml of water and 6.0 ml of THF and heated with stirring to 50° C. A solution of maleic acid in 4 ml of THF was added to the reaction mixture and the mixture was stirred for 30 minutes. After cooling to room temperature and agitating for 2 hours the thus formed solid was filtered, washed with 2×5 ml of cold THF and dried under reduced pressure at 50° C. to afford midazolam maleate in 85.6% yield having purity of 99.87%, containing 0.033% of compound VIII and 0.072% of compound IX (according to HPLC).

Examples 5-10

This example describes the purification of midazolam maleate containing 0.76% of Compound IX before crystallization.

The following examples describe the purification of midazolam maleate, containing 0.76% of Compound IX before crystallization, by crystallization from different solvent mixtures, as detailed in Table 2. The general procedure for crystallization was the following: the midazolam maleate was placed in a reaction vessel, equipped with a reflux condenser and a mixer, and the solvents were added at the specific volume ratio as detailed in Table 2, and the mixture was heated to reflux, after which time it was left to cool under gentle stirring. The thus formed crystals were obtained by filtration, dried and a sample was withdrawn, diluted with a mixture of water and acetonitrile, and injected to the HPLC system.

TABLE 2

| Entry | Solvent mixture (v/v) | Midazolam maleate:solvent ratio, g/ml | Yield, % | Purity %, by HPLC | % of IX after crystallization |
|---|---|---|---|---|---|
| 5 | THF:ethanol, 2.94:1 | 1:5 | 89.4 | 99.8% | 0.08 |
| 6 | THF:ethanol, 1:1 | 1:5.5 | 70.5 | 99.9% | 0.04 |
| 7 | THF:ethanol, 1.5:1 | 1:6 | 80.0 | 99.7% | 0.10 |
| 8 | THF:2-propanol, 1.5:1 | 1:6 | 84.7 | 99.8% | 0.04 |
| 9 | THF:2-propanol, 2:1 | 1:6 | 86.8 | 99.8% | 0.07 |
| 10 | THF:2-propanol, 1.5:1 | 1:6 | 86.0 | 99.8% | 0.08 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for purifying midazolam base containing impurities of formulae VIII and XI:

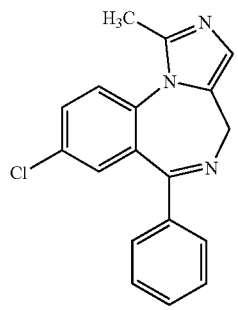

VIII

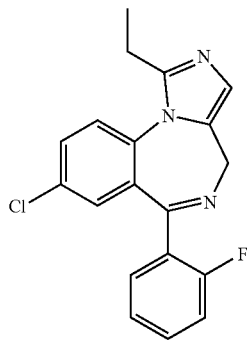

IX the process comprising:
   (a) precipitating the midazolam base from a solvent containing water and a $C_{1-3}$ alkyl acetate, and isolating the precipitated midazolam base to substantially remove the impurity of formula VIII; and
   (b) converting the midazolam produced in step (a) into the maleate salt, precipitating the maleate salt from a solvent comprising tetrahydrofuran (THF), and isolating the midazolam maleate, to substantially remove the impurity of formula IX.

2. The process of claim 1, wherein step (a) comprises dissolving the midazolam base in the solvent at elevated temperature; allowing the solution to cool sufficiently to produce crystals of midazolam base; and isolating the midazolam base crystals.

3. The process of claim 2, wherein the $C_{1-3}$ alkyl acetate is methyl acetate, ethyl acetate, isopropyl acetate or a mixture thereof.

4. The process of claim 3, wherein the $C_{1-3}$ alkyl acetate is methyl acetate or ethyl acetate.

5. The process of claim 4, wherein the ratio between the midazolam base and the solvent in step (a) is about 1 g midazolam base per about 1-7 ml solvent.

6. The process of claim 2, further comprising washing the midazolam base micrystals with acetone, tetrahydrofuran (THF), methyl acetate, ethyl acetate, isopropyl acetate, n-butyl acetate, isobutyl acetate, cyclohexane, or a mixture thereof.

7. The process of claim 6, wherein the solvent used for washing the midazolam base crystals is a mixture of cyclohexane and methyl acetate with a ratio of about 7:3 (v/v) cyclohexane:methyl acetate.

8. The process of claim 2, wherein the midazolam base crystals obtained in step (a) contain less than about 0.2% of the impurity of formula VIII.

9. The process of claim 8, wherein the midazolam base crystals obtained in step (a) contain less than about 0.07% of the impurity of formula VIII.

10. The process of claim 1, wherein the midazolam base produced in step (a) is crystalline, and step (b) comprises dissolving the crystalline midazolam base in a solvent comprising tetrahydrofuran (THF) at elevated temperature, adding a solution of maleic acid in a solvent to produce midazolam maleate, allowing the mixture to cool sufficiently to produce midazolam maleate crystals, and isolating the midazolam maleate crystals.

11. The process of claim 10, wherein the solvent used in step (b) for dissolving the midazolam base further comprises water, methanol, ethanol, 1-propanol, 2-propanol, 1-butanol, 2-butanol, acetone, or a mixture thereof.

12. The process of claim 11, wherein the solvent used in step (b) for dissolving the midazolam base is a mixture of THF and water with a ratio of about 25:1 (v/v) THF:water.

13. The process of claim 12, wherein step (b) comprises adding maleic acid as a solution in methanol, ethanol, 1-propanol, 2-propanol, 1-butanol, 2-butanol, tetrahydrofuran (THF), 2-methyltetrahydrofuran, acetonitrile, N,N-dimethylformamide (DMF), dimethylacetamide (DMA), dimethylsulfoxide (DMSO), or a mixture thereof.

14. The process of claim 13, wherein step (b) comprises adding maleic acid as a solution in THF.

15. The process of claim 10, wherein the midazolam maleate produced in step (b) has a purity of at least about 98.5%.

16. The process of claim 15, wherein the midazolam maleate produced in step (b) has a purity of at least about 99.5%.

17. The process of claim 10, wherein the midazolam maleate produced in step (b) contains less than about 0.1% of the impurity of formula VIII, and less than about 0.1% of the impurity of formula IX.

\* \* \* \* \*